(12) United States Patent
Kobayashi et al.

(10) Patent No.: US 10,575,812 B2
(45) Date of Patent: Mar. 3, 2020

(54) CONTROL DEVICE, RADIATION IMAGING APPARATUS, RADIATION IMAGING METHOD, AND RADIATION IMAGING PROGRAM

(71) Applicant: FUJIFILM Corporation, Tokyo (JP)

(72) Inventors: Takeyasu Kobayashi, Kanagawa (JP); Naokazu Kamiya, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 202 days.

(21) Appl. No.: 15/923,192

(22) Filed: Mar. 16, 2018

(65) Prior Publication Data

US 2018/0199906 A1 Jul. 19, 2018

Related U.S. Application Data

(63) Continuation of application No. PCT/JP2016/060996, filed on Apr. 4, 2016.

(30) Foreign Application Priority Data

Sep. 29, 2015 (JP) .................. 2015-192290

(51) Int. Cl.
*A61B 6/02* (2006.01)
*A61B 6/03* (2006.01)
(Continued)

(52) U.S. Cl.
CPC .............. *A61B 6/5264* (2013.01); *A61B 6/00* (2013.01); *A61B 6/025* (2013.01); *A61B 6/04* (2013.01);
(Continued)

(58) Field of Classification Search
CPC ....... A61B 6/502; A61B 6/035; A61B 6/4435; A61B 6/06; G06T 2207/30068; G06T 7/0012
See application file for complete search history.

(56) References Cited

U.S. PATENT DOCUMENTS

| 6,611,575 B1 | 8/2003 | Alyassin et al. |
| 2008/0165916 A1 | 7/2008 | Stanton et al. |
| (Continued) |

FOREIGN PATENT DOCUMENTS

| DE | 10 2013 203998 A1 | 9/2014 |
| JP | 2004-188200 A | 7/2004 |
| (Continued) |

OTHER PUBLICATIONS

Notification of Reasons for Refusal dated Mar. 19, 2019 from the Japanese Patent Office in application No. 2017-542767.
(Continued)

*Primary Examiner* — Don K Wong
(74) *Attorney, Agent, or Firm* — Sughrue Mion, PLLC

(57) ABSTRACT

A control unit of a radiation imaging apparatus performs control of moving a radiation source, and emitting radiation from the radiation source at a plurality of positions at which incidence angles of the radiation to a breast of a subject are different from each other. The control unit performs control of causing a radiation detector to detect the radiation emitted from the radiation source at the plurality of positions. The control unit performs control of moving the radiation source at a movement speed corresponding to a position of the radiation source for a subject face proximate position.

20 Claims, 11 Drawing Sheets

(51) Int. Cl.
  *A61B 6/00* (2006.01)
  *A61B 6/10* (2006.01)
  *A61B 6/04* (2006.01)
(52) U.S. Cl.
  CPC .............. *A61B 6/0414* (2013.01); *A61B 6/10* (2013.01); *A61B 6/107* (2013.01); *A61B 6/4028* (2013.01); *A61B 6/502* (2013.01); *A61B 6/547* (2013.01)

(56) References Cited

U.S. PATENT DOCUMENTS

| | | |
|---|---|---|
| 2009/0135995 A1 | 5/2009 | Eberhard et al. |
| 2009/0304147 A1 | 12/2009 | Jing et al. |
| 2012/0114095 A1 | 5/2012 | Smith et al. |
| 2012/0195403 A1* | 8/2012 | Vedantham ............ A61B 6/022 378/4 |
| 2012/0219109 A1 | 8/2012 | Albanese et al. |
| 2013/0331682 A1 | 12/2013 | Ohta et al. |
| 2014/0198896 A1 | 7/2014 | Hemmendorff et al. |
| 2015/0201890 A1 | 7/2015 | Maidment et al. |

FOREIGN PATENT DOCUMENTS

| | | |
|---|---|---|
| JP | 2006-231054 A | 9/2006 |
| JP | 2007-050264 A | 3/2007 |
| JP | 2008-148866 A | 7/2008 |
| JP | 2011-072501 A | 4/2011 |
| JP | 2012-024424 A | 2/2012 |
| JP | 2012-175997 A | 9/2012 |
| JP | 2013-538668 A | 10/2013 |
| JP | 2017-012448 A | 1/2017 |
| JP | 2017-060559 A | 3/2017 |

OTHER PUBLICATIONS

International Search Report for PCT/JP2016/060996 dated Jun. 21, 2016.
International Preliminary Report on Patentability with the translation of Written Opinion dated Apr. 3, 2018 issued by the International Bureau in No. PCT/JP2016/060996.
Communication from European Patent Office dated Sep. 17, 2018 issued in corresponding European Application No. EP16850710.1.

* cited by examiner

CONTROL DEVICE, RADIATION IMAGING APPARATUS, RADIATION IMAGING METHOD, AND RADIATION IMAGING PROGRAM

CROSS-REFERENCE TO RELATED APPLICATIONS

This application is a Continuation of PCT International Application No. PCT/JP2016/060996 filed on Apr. 4, 2016, which claims priority under 35 U.S.C. § 119(a) to Japanese Patent Application No. 2015-192290 filed on Sep. 29, 2015. Each of the above application(s) is hereby expressly incorporated by reference, in its entirety, into the present application.

BACKGROUND OF THE INVENTION

1. Field of the Invention

The present invention relates to a control device of a mammography, a mammography, a radiation imaging method of a mammography, and a non-transitory computer readable recording medium storing a radiation imaging program of a mammography.

2. Description of the Related Art

Generally, there is a radiation imaging apparatus which performs radiation imaging for the purpose of medical diagnosis or the like. In such a radiation imaging apparatus, a technique of performing tomosynthesis imaging or stereo imaging is known in which radiation is applied to an object from a plurality of different incidence angles, and radiation imaging is performed at each incidence angle. In the tomosynthesis imaging or the stereo imaging, radiation is applied to an object from a plurality of different incidence angles, and thus a radiation source is moved in a state in which the object is positioned.

There is a mammography as a radiation imaging apparatus which captures a radiation image with the breast of a subject as an object. In a case of performing tomosynthesis imaging or stereo imaging in the mammography, movement of a radiation source may influence a subject. Thus, a technique of suppressing the influence which is exerted on a subject due to the movement of a radiation source is desirable. As such a technique, for example, JP2012-175997A discloses a technique in which, in a case where the face of a subject comes into contact with a face guard which is a shield member preventing the face of the subject from being irradiated with radiation, a radiation source is relatively moved for the face guard. In the technique disclosed in JP2012-175997A, the radiation source is moved in a state in which the face of the subject is in contact with the face guard such that an attitude of the body of the subject is stabilized, and thus the attitude of the body of the subject is prevented from being unstable due to the movement of the radiation source.

SUMMARY OF THE INVENTION

In a case where a radiation source is moved in the mammography, the radiation source is generally moved in a location close to the face of a subject. Thus, in some cases, the subject unconsciously reacts to the movement of the radiation source, and thus the body thereof moves (body motion occurs). In the related art described above, an attitude of the body of the subject is stabilized, but it is difficult to suppress an unconscious reaction of the subject.

In a case where a radiation image such as a reconstructed image is generated by using a radiation image captured in a state in which body motion of a subject occurs, image quality of the generated radiation image deteriorates. In a case where a radiation image such as a reconstructed image is generated without using a radiation image captured in a state in which body motion of a subject occurs, the number of radiation images for generation thereof is reduced, and thus image quality of the generated radiation image deteriorates.

The present invention has been made in consideration of the circumstances, and an object thereof is to provide a control device of a mammography, a mammography, a radiation imaging method of a mammography, and a non-transitory computer readable recording medium storing a radiation imaging program of a mammography, capable of suppressing deterioration in image quality of a radiation image due to body motion of a subject.

In order to achieve the above object, according to the present invention, there is provided a control device of a mammography comprising a ray source control unit that performs control of moving a radiation source, and emitting radiation from the radiation source at a plurality of positions at which incidence angles of radiation to a breast of a subject are different from each other; and a detector control unit that performs control of causing a radiation detector to detect radiation emitted from the radiation source at the plurality of positions, in which the ray source control unit performs control of moving the radiation source at a movement speed corresponding to a position of the radiation source relative to a subject face proximate position.

The "subject face proximate position" is a position at which the radiation source comes close to the face of the subject in a case where the radiation source is moved. Specifically, a position of the radiation source (for example, a position of the radiation source at which an emission direction of radiation is a normal direction to the detection surface of the radiation detector) expected to come close to the face of the subject may be defined in advance as the subject face proximate position. Alternatively, a position of the face of the subject may be detected, and a position of the radiation source close to the position may be obtained as the subject face proximate position. The proximate position is not limited to the most proximate position, and may be a position deviated from the most proximate position to the extent of a width of the face.

The ray source control unit of the control device of the mammography of the present invention may perform control of the movement speed of the radiation source, such that the movement speed of the radiation source or a change amount of the movement speed per unit time is less at a position of the radiation source that has been predefined as a position near the subject face proximate position than at other positions.

The ray source control unit of the control device of the mammography of the present invention may perform the control such that speed change patterns of the radiation source are different from each other at the predefined position of the radiation source and other positions.

The control device of the mammography of the present invention may further comprise a position detection unit that detects a position of the face of the subject, and the ray source control unit may change the movement speed of the radiation source according to a position of the radiation source for the position of the face of the subject on the basis of a detection result in the position detection unit, and move the radiation source.

The ray source control unit of the control device of the mammography of the present invention may set the plurality of positions to positions corresponding to a plurality of angles including a first angle as an angle of a normal direction to a detection surface of the radiation detector and a second angle which is different from the first angle.

In a case where the movement speed is changed, the ray source control unit of the control device of the mammography of the present invention may perform control of the movement speed of the radiation source, such that the movement speed of the radiation source or a change amount of the movement speed per unit time is less in a case where the radiation source is located at a position within a predetermined range which has been predefined and in which the incidence angle includes the first angle than in a case where the radiation source is located at other positions.

The ray source control unit of the control device of the mammography of the present invention may perform the control such that a speed change pattern of the radiation source in a case where the radiation source is located at the position within the predetermined range is different from a speed change pattern of the radiation source in a case where the radiation source is located at other positions.

In a case where the movement speed is changed by changing a change amount of the movement speed per unit time, the ray source control unit of the control device of the mammography of the present invention may set an absolute value of the change amount in a case where acceleration is performed to be smaller than an absolute value of the change amount in a case where deceleration is performed.

The control device of the mammography of the present invention may further comprise a direction detection unit that detects a direction of the face of the subject, and the ray source control unit may perform at least one of control of the movement speed on the basis of a detection result in the direction detection unit such that the movement speed is less in a direction in which the face of the subject is directed than in a direction in which the face of the subject is not directed, or control of setting an absolute value of a change amount in a case where acceleration is performed in a direction in which the face of the subject is directed to be smaller than an absolute value of the change amount in a case where deceleration is performed in a direction in which the face of the subject is not directed if the movement speed is changed by changing the change amount of the movement speed per unit time.

The ray source control unit of the control device of the mammography of the present invention may stop movement of the radiation source at each imaging position corresponding to the incidence angle of the radiation source.

According to the present invention, there is provided a mammography comprising a radiation source that irradiates an object with radiation; a radiation detector that captures a radiation image of the object on the basis of radiation having been transmitted through the object; and the control device of the mammography of the present invention.

According to the present invention, there is provided a radiation imaging method of a mammography of causing a computer to execute a process comprising performing control of moving a radiation source, and emitting radiation from the radiation source at a plurality of positions at which incidence angles of radiation to a breast of a subject are different from each other; performing control of causing a radiation detector to detect radiation emitted from the radiation source at the plurality of positions; and performing control of moving the radiation source at a movement speed corresponding to a position of the radiation source relative to a subject face proximate position.

According to the present invention, there is provided a non-transitory computer readable recording medium storing a radiation imaging program of a mammography for causing a computer to execute a process comprising performing control of moving a radiation source, and emitting radiation from the radiation source at a plurality of positions at which incidence angles of radiation to a breast of a subject are different from each other; performing control of causing a radiation detector to detect radiation emitted from the radiation source at the plurality of positions; and performing control of moving the radiation source at a movement speed corresponding to a position of the radiation source relative to a subject face proximate position.

According to the present invention, it is possible to provide a control device of the mammography, a mammography, a radiation imaging method of a mammography, and a non-transitory computer readable recording medium storing a radiation imaging program of a mammography, capable of suppressing deterioration in image quality of a radiation image due to body motion of a subject.

DESCRIPTION OF THE PREFERRED EMBODIMENTS

Hereinafter, embodiments of the present invention will be described in detail with respect to the drawings. The present embodiments do not limit the present invention. Hereinafter, the term "same" includes an allowable error range.

First Embodiment

Figure 1:
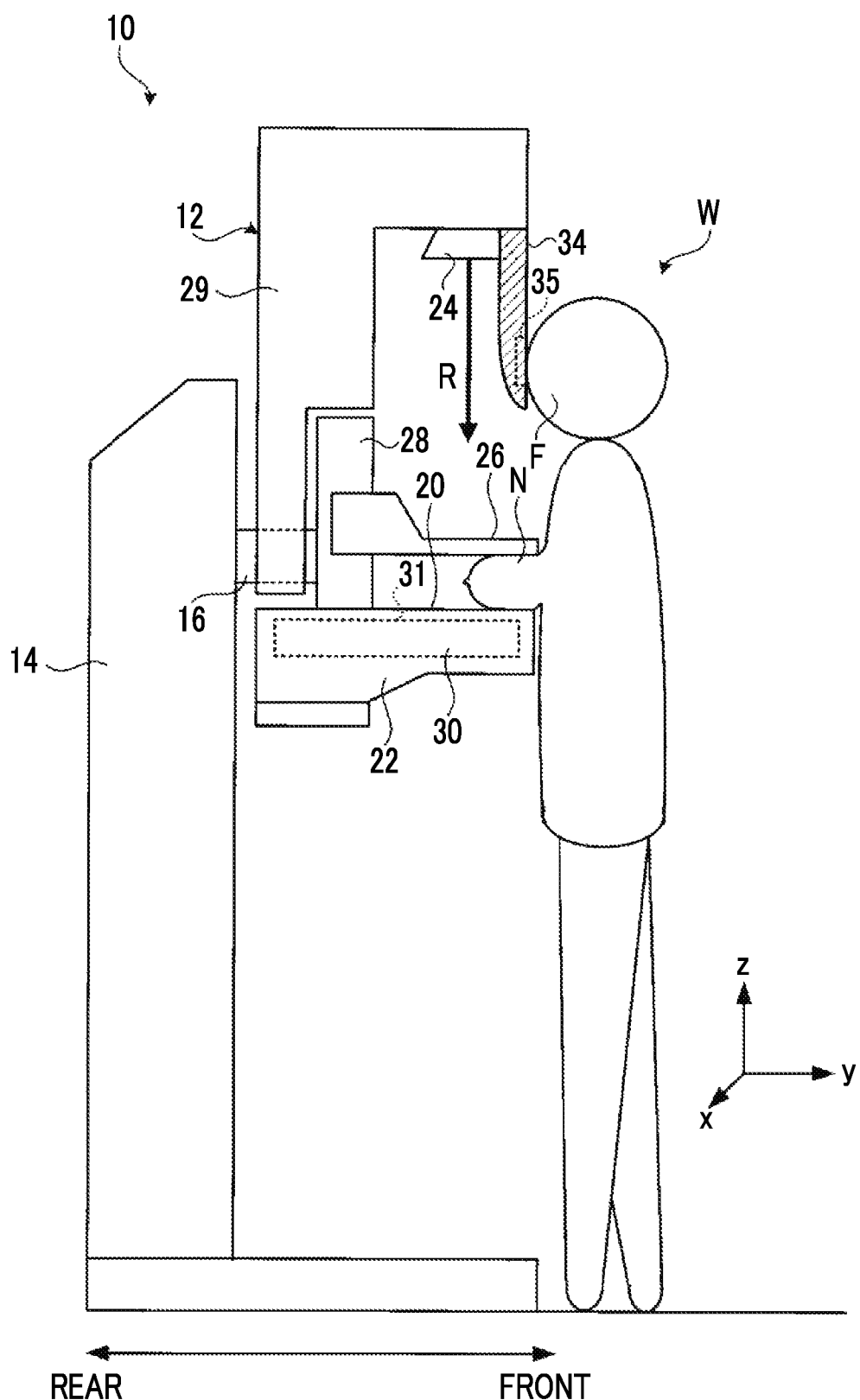
FIG. 1 is a side view illustrating a configuration example of a radiation imaging apparatus according to a first embodiment.
Figure 2:
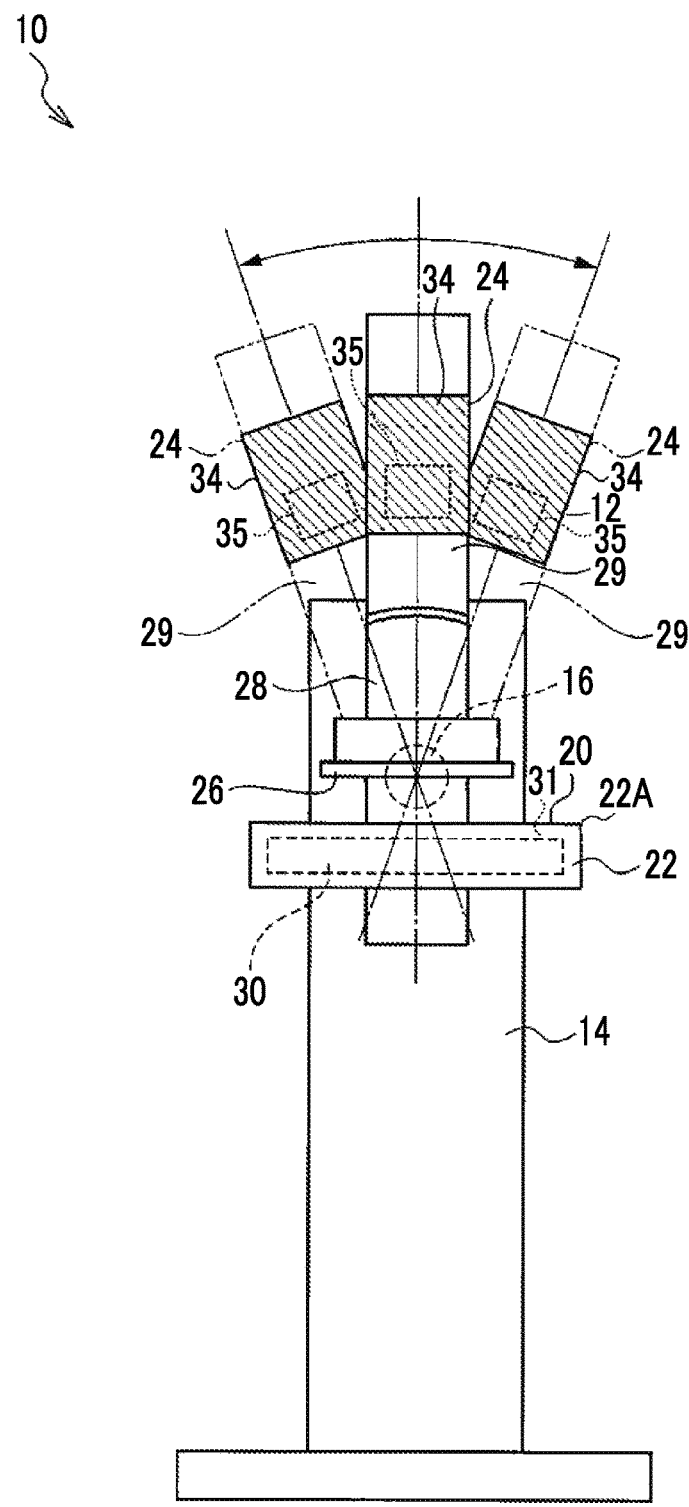
FIG. 2 is a front view illustrating a configuration example of the radiation imaging apparatus illustrated in FIG. 1.
Figure 3:
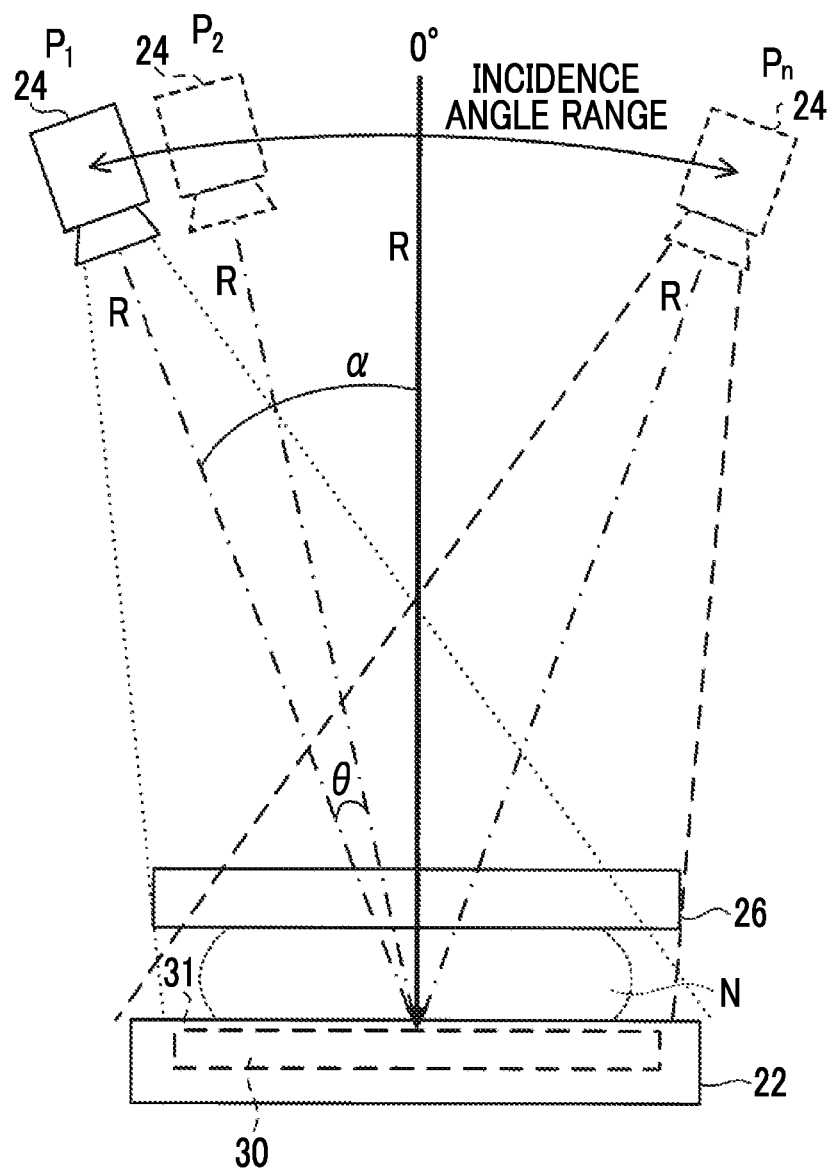
FIG. 3 is a diagram for explaining tomosynthesis imaging in the radiation imaging apparatus according to the first embodiment.

First, a radiation imaging apparatus of the present embodiment will be described. As illustrated in FIGS. 1 to 3, a radiation imaging apparatus 10 of the present embodiment is an apparatus performing imaging using radiation R (for example, X-rays) with the breast N of a subject W as an object in a state in which the subject W stands. A specific example of the radiation imaging apparatus 10 may include a mammography. Hereinafter, a description will be made assuming that a side close to the subject W in a case where the subject W faces the radiation imaging apparatus 10 during imaging is set to an apparatus front side, a side separated from the subject W in a case where the subject W faces the radiation imaging apparatus 10 during imaging is set to an apparatus rear side, and a leftward-and-rightward direction of the subject W in a case where the subject W faces the radiation imaging apparatus 10 during imaging is set to an apparatus leftward-and-rightward direction (refer to each arrow in FIGS. 1 and 2).

The radiation imaging apparatus 10 may be an apparatus imaging the breast N of the subject W in a sitting state in which the subject W sits on a chair (including a wheelchair).

As illustrated in FIG. 1, the radiation imaging apparatus 10 includes a measurement section 12 which has a substantially C shape in a side view and is provided on the apparatus front side, and a base section 14 supporting the measurement section 12 from the apparatus rear side.

The measurement section 12 includes an imaging table 22 provided with a planar imaging surface 20 which comes into contact with the breast N of the standing subject W, a compression plate 26 which compresses the breast N along with the imaging surface 20 of the imaging table 22, and a holding unit 28 which supports the imaging table 22 and the compression plate 26. A member through which the radiation R is transmitted is used for the compression plate 26.

The measurement section 12 includes a face guard 34 which is formed by using a member shielding the radiation R in order to protect the vicinity of the face of the subject W from exposure to the radiation R. The face guard 34 is provided with a face position detection sensor 35, and the face position detection sensor 35 detects a position of the face F of the subject W facing the face guard 34. The face position detection sensor 35 of the present embodiment uses a sensor which captures an image of the face F (hereinafter, referred to as a "face image") of the subject W by using imaging elements as an example, and detects a position of the face F of the subject W on the basis of the captured face image. The face position detection sensor 35 of the present embodiment is an example of a position detection unit of the present invention.

The measurement section 12 includes a radiation source 24 which includes a tube bulb or the like and irradiates the breast N with the radiation R, and a support unit 29 which supports the radiation source 24 separately from the holding unit 28.

The measurement section 12 is provided with a shaft 16, and thus the measurement section 12 can be rotated with respect to the base section 14. The shaft 16 is fixed to the support unit 29, and the shaft 16 and the support unit 29 are integrally rotated.

The shaft 16 and the holding unit 28 are respectively provided with gears, and can switch between a state in which the holding unit 28 and the shaft 16 are connected to each other and are integrally rotated, and a state in which the shaft 16 is separated from the holding unit 28 so as to be idly rotated, by performing switching between an engagement state and a non-engagement state of the gears. Switching between transmission and non-transmission of power to the shaft 16 is not limited to the gears, and may be performed by using various mechanical elements.

The holding unit 28 supports the imaging table 22 and the radiation source 24 such that the imaging surface 20 and the radiation source 24 are separated from each other with a predetermined interval. The holding unit 28 also holds the compression plate 26, and the compression plate 26 is slidably moved in the holding unit 28, so that a gap between the compression plate 26 and the imaging surface 20 is changed.

The imaging surface 20 coming into contact with the breast N is made of, for example, carbon from the viewpoint of radiation transmittance or intensity. A radiation detector 30 which detects the radiation R passing through the breast N and the imaging surface 20 is provided inside the imaging table 22. A radiation image is generated on the basis of the radiation R detected by the radiation detector 30. The type of radiation detector 30 of the present embodiment is not particularly limited, and may be, for example, an indirect conversion type radiation detector which converts the radiation R into light, and converts the converted light into electric charge, and may be a direct conversion type radiation detector which directly converts the radiation R into electric charge.

As illustrated in FIGS. 2 and 3, the radiation imaging apparatus 10 of the present embodiment may apply the radiation R at different incidence angles of the radiation R applied from the radiation source 24 within a predetermined range, and may perform imaging (so-called tomosynthesis imaging) at the different incidence angles. Here, the "incidence angle" indicates an angle formed between a normal line to a detection surface 31 of the radiation detector 30 and a radiation axis. Therefore, in a case where a normal line is the same as a radiation axis, an incidence angle is 0 degrees. Herein, the detection surface 31 of the radiation detector 30 is substantially parallel to the imaging surface 20.

Hereinafter, a range in which incidence angles in tomosynthesis imaging is performed once is referred to as an "incidence angle range". Examples of the incidence angle range may include ±10 degrees or ±20 degrees with respect to the normal line to the detection surface 31 of the radiation detector 30. Each radiation image captured in the tomosynthesis imaging is referred to as a "projection image".

In the present embodiment, as illustrated in FIG. 3, imaging is performed at n positions (imaging positions) from $P_1$ to $P_n$ as a position of the radiation source 24 by moving a position of the radiation source 24 from an angle α by a predetermined angle θ.

In the radiation imaging apparatus 10 of the present embodiment, imaging is performed at each imaging position while consecutively moving the radiation source 24. In an imaging method of consecutively moving the radiation source 24, for example, the radiation source 24 may irradiate the breast N with the radiation R in a case of reaching each imaging position without being stopped while the radiation source 24 is moved, and the radiation detector 30 may perform imaging in synchronization with the timing of the irradiation.

Next, a description will be made of a configuration of a radiation imaging system 1 of the present embodiment.

Figure 4:
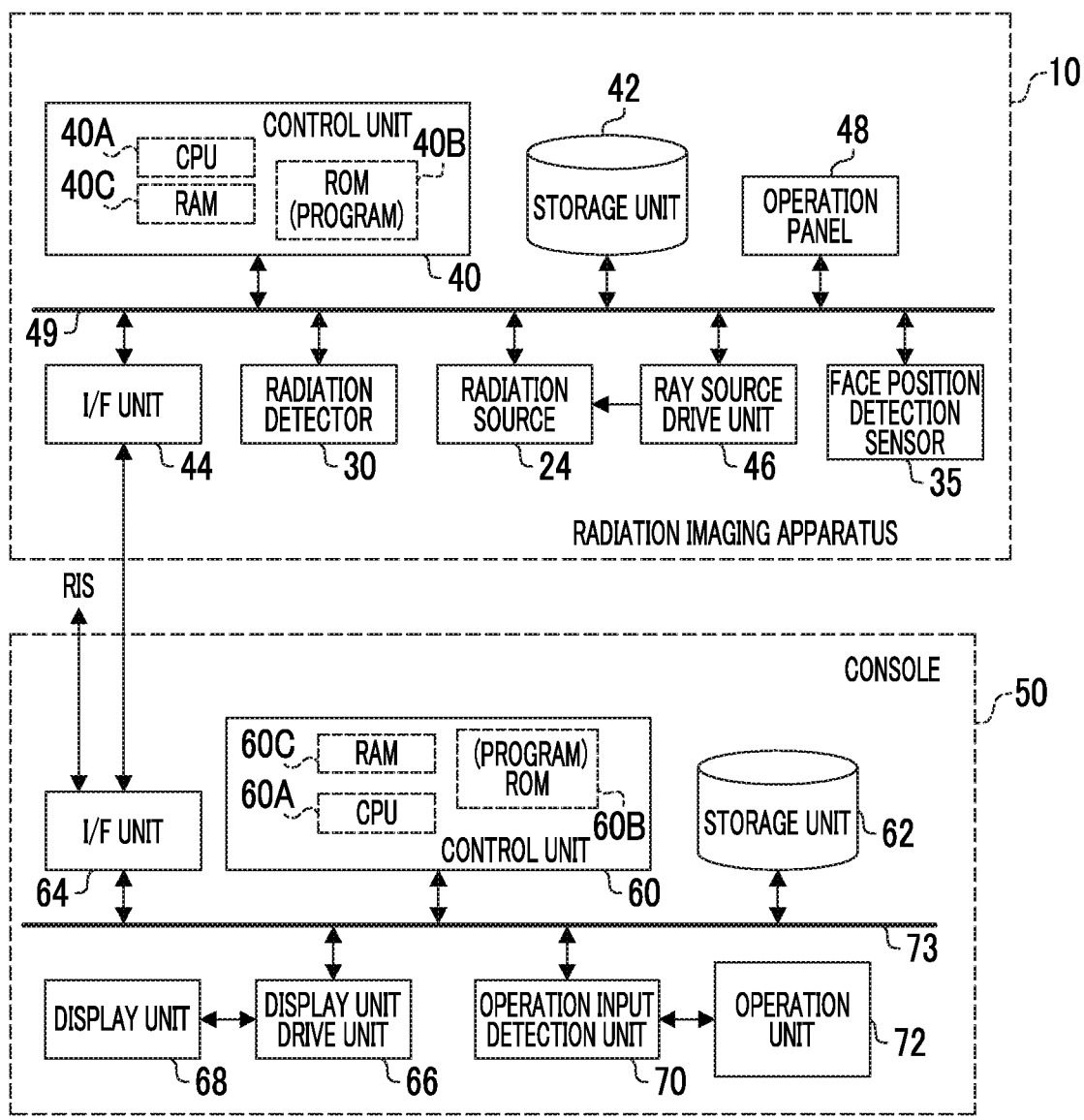
FIG. 4 is a block diagram illustrating a configuration example of a radiation imaging system according to the first embodiment.

FIG. 4 is a block diagram illustrating an example of a configuration of the radiation imaging system 1 of the present embodiment. As illustrated in FIG. 4, the radiation imaging system 1 of the present embodiment includes the radiation imaging apparatus 10 and a console 50.

The console 50 controls the radiation imaging apparatus 10 by using an imaging menu acquired from an external system or the like via a wireless communication local area network (LAN) or the like, or other various pieces of information.

The console 50 of the present embodiment is a server computer. As illustrated in FIG. 4, the console 50 includes a control unit 60, a storage unit 62, an interface (I/F) unit 64, a display unit drive unit 66, a display unit 68, an operation input detection unit 70, and an operation unit 72. The control unit 60, the storage unit 62, the IF unit 64, the display unit drive unit 66, and the operation input detection unit 70 are connected to each other so as to transmit and receive various pieces of information via a bus 73 such as a system bus or a control bus.

The control unit 60 of the present embodiment controls an operation of the entire console 50. The control unit 60 of the present embodiment includes a central processing unit (CPU) 60A, a read only memory (ROM) 60B, and a random access memory (RAM) 60C. The ROM 60B stores various processing programs or the like executed in the CPU 60A in advance. The RAM 60C temporarily stores various pieces of data.

The storage unit 62 stores image data of a radiation image captured in the radiation imaging apparatus 10, or other various pieces of information. Specific examples of the storage unit 62 may include a hard disk drive (HDD) or a solid state drive (SSD).

The I/F unit 64 performs communication of various pieces of information with the radiation imaging apparatus 10 or an external system (radiology information system (RIS)) via wireless communication or wired communication.

The display unit 68 displays various pieces of information. The display unit drive unit 66 controls display of various pieces of information on the display unit 68.

The operation unit 72 is used for a user to input instructions regarding capturing of a radiation image, including an instruction for exposure of the radiation R. or various pieces of information. In the present embodiment, a radiologist or a doctor performing imaging by using the radiation imaging system 1 (radiation imaging apparatus 10) is referred to as a "user".

The operation unit 72 is not particularly limited, and may be, for example, various switches, a touch panel, a touch pen, and a mouse. The operation unit 72 and the display unit 68 may be integrally formed to be used as a touch panel display. The operation input detection unit 70 detects an operation state on the operation unit 72.

On the other hand, the radiation imaging apparatus 10 of the present embodiment includes the radiation source 24, the radiation detector 30, the face position detection sensor 35, a control unit 40, a storage unit 42, an I/F unit 44, a ray source drive unit 46, and an operation panel 48. In the present embodiment, as an example, the radiation imaging apparatus 10 has a function of a control device of the present invention.

The radiation source 24, the radiation detector 30, the face position detection sensor 35, the control unit 40, the storage unit 42, the I/F unit 44, the ray source drive unit 46, and the operation panel 48 are connected to each other so as to transmit and receive various pieces of information via a bus 49 such as a system bus or a control bus.

The control unit 40 of the present embodiment controls an operation of the entire radiation imaging apparatus 10. The control unit 40 of the present embodiment controls the radiation source 24 and the radiation detector 30 in a case where a radiation image is captured. The control unit 40 of the present embodiment includes a CPU 40A, a ROM 40B, and a RAM 40C. The ROM 40B stores various programs or the like including an imaging process program which will be described later, executed in the CPU 40A in advance. The RAM 40C temporarily stores various pieces of data. In the radiation imaging system 1 of the present embodiment, the CPU 40A executes the imaging process program stored in the ROM 40B, and thus the control unit 40 functions as a ray source control unit and a detector control unit. The imaging process program of the present embodiment is an example of a radiation imaging program of the present embodiment.

The storage unit 42 stores image data of a radiation image captured in the radiation detector 30, or other various pieces of information. Specific examples of the storage unit 42 may include an HDD or an SSD.

The I/F unit 44 performs communication of various pieces of information with the console 50 via wireless communication or wired communication.

In the present embodiment, various programs stored in the control unit 40 of the radiation imaging apparatus 10 and the control unit 60 of the console 50 are stored in the ROMs (40B and 60B) of the control unit 40 and the control unit 60 in advance, but are not limited thereto. The various programs may be stored in, for example, a recording medium such as a compact disk read only memory (CD-ROM) or a removable disc, and may be installed to the ROMs (40B and 60B) from the recording medium. The programs may be installed to the ROMs (40B and 60B) from an external device via a communication line such as the Internet.

The ray source drive unit 46 moves the radiation source 24 to a position corresponding to an incidence angle by rotating the shaft 16. In the radiation imaging apparatus 10 of the present embodiment, the face guard 34 is also moved according to movement of the radiation source 24.

The operation panel 48 has a function of receiving a compression instruction for a user moving up and down the compression plate 26 such that the breast N of the subject W is interposed. The operation panel 48 is provided with, for example, a plurality of switches on the imaging table 22 of the radiation imaging apparatus 10. The operation panel 48 may be provided with a touch panel.

Next, a description will be made of an operation of the radiation imaging apparatus 10 of the present embodiment with reference to the drawings.

First, a description will be made of an imaging process performed in the radiation imaging apparatus 10 of the radiation imaging system 1 of the present embodiment.

In the radiation imaging system 1 of the present embodiment, in a case where the breast N of the subject W starts to be imaged, the user gives an instruction for starting imaging by using the operation unit 72 of the console 50. The instruction for starting imaging which is input via the operation unit 72 is detected by the operation input detection unit 70, and is transmitted to the radiation imaging apparatus 10 via the I/F unit 64. The user positions the breast N of the subject W on the imaging surface 20 of the imaging table 22 of the radiation imaging apparatus 10. In the radiation imaging apparatus 10 of the present embodiment, in a case where tomosynthesis imaging or Cranio-Caudal (CC) imaging is performed, positioning is performed in a state in which the imaging surface 20 of the imaging table 22 is brought into a lower side of the breast N of the subject W. and a position of the radiation source 24 is a position at which an incidence angle is 0 degrees. In this case, a position of the face F of the subject W is a position facing the face guard 34.

Figure 5:
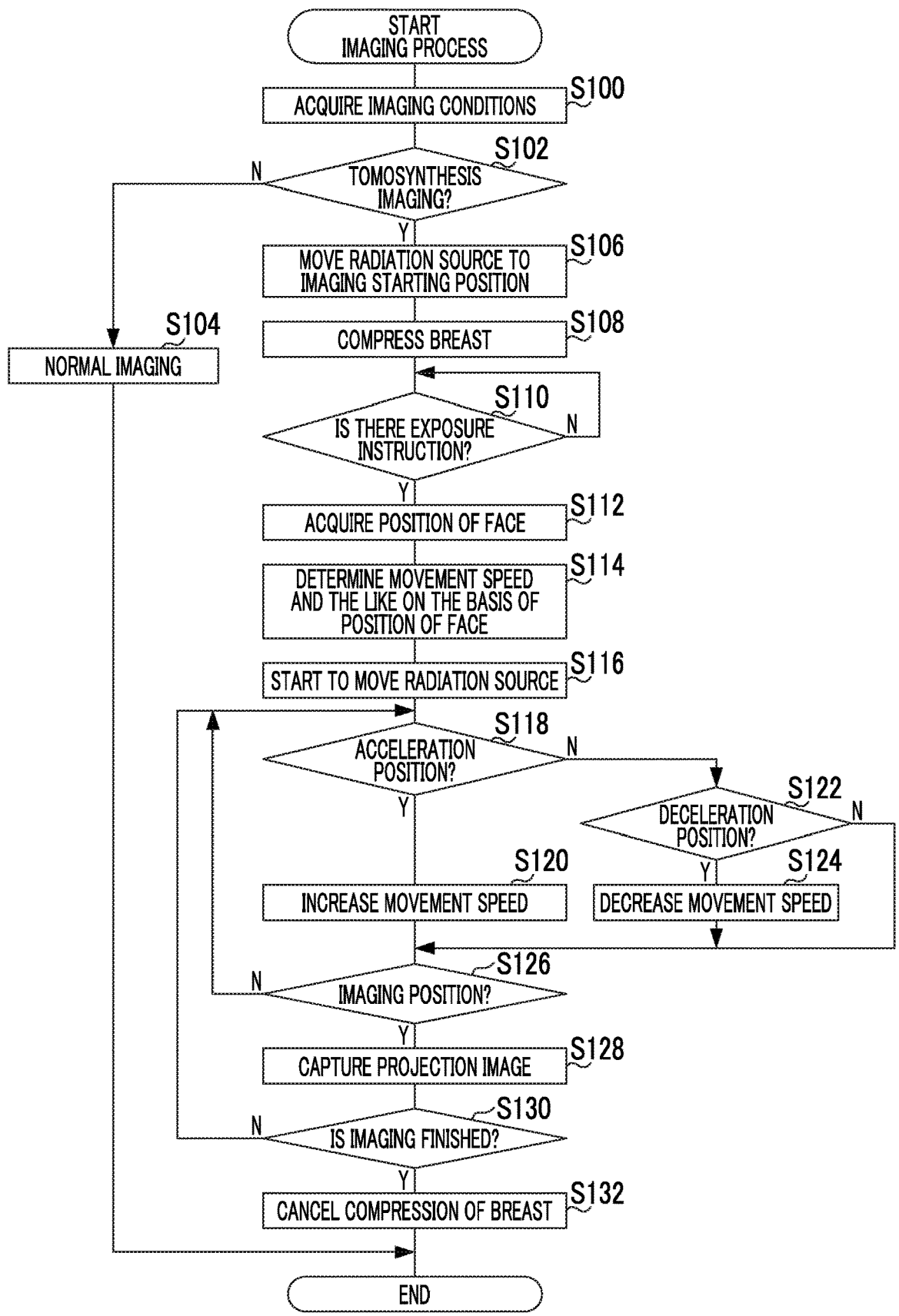
FIG. 5 is a flowchart illustrating an example of an imaging process performed in the radiation imaging apparatus according to the first embodiment.

In the radiation imaging apparatus 10 of the present embodiment, in a case where an instruction for starting capturing of a radiation image is received from the console 50 via the I/F unit 44, an imaging process is performed. FIG. 5 is a flowchart illustrating an example of an imaging process performed by the control unit 40 of the radiation imaging apparatus 10 of the present embodiment. In the radiation imaging apparatus 10 of the present embodiment, the CPU 40A of the control unit 40 executes the imaging process program stored in the ROM 40B, and thus the imaging process is performed.

In step S100, the control unit 40 acquires imaging conditions. The imaging conditions include information indicating whether the type of imaging is tomosynthesis imaging or normal imaging (which will be described later in detail), exposure conditions of the radiation R in the radiation source 24 including, for example, a tube voltage, a tube current, an irradiation time, and a dose, and information regarding capturing of a radiation image, such as attitude information. The attitude information in the present embodiment is information regarding an attitude of the radiation source 24, and includes information indicating an imaging position (including an incidence angle and an incidence angle range) of the radiation source 24 in a case where tomosynthesis imaging is performed on the breast N.

The imaging conditions are included in an imaging menu along with subject information regarding the subject W or the breast N. Thus, in a case where the console 50 acquires the imaging menu from an RIS or the like, the control unit 40 acquires the imaging conditions from the console 50 via the I/F unit 44. Also in a case where the user sets imaging conditions by using the operation unit 72 or the like of the console 50, the control unit 40) acquires the imaging conditions from the console 50 via the I/F unit 44.

In a case where the imaging conditions are stored in the storage unit 42 of the radiation imaging apparatus 10 in advance, the control unit 40 may acquire the imaging conditions from the storage unit 42.

In the next step S102, the control unit 40 determines whether or not the tomosynthesis imaging is to be performed on the basis of the imaging conditions. In a case where it is determined that the tomosynthesis imaging is not to be performed, the normal imaging is performed, so that a negative determination is performed, and thus the flow proceeds to step S104.

In step S104, the control unit 40 performs the normal imaging, and then finishes the imaging process. In the present embodiment, the normal imaging indicates that, unlike the tomosynthesis imaging, the radiation source 24 irradiates the breast N with the radiation R in a state in which an incidence angle is fixed without moving the radiation source 24 during imaging, and a radiation image is captured. An example of the normal imaging may include CC imaging or medio-lateral oblique (MLO) imaging.

Although the normal imaging is not described in detail, the breast N is compressed with the compression plate 26, the radiation R is applied to the breast N from the radiation source 24 on the basis of imaging conditions, a radiation image is captured by the radiation detector 30, and then compression of the breast N is canceled.

On the other hand, in a case where it is determined that the tomosynthesis imaging is to be performed in step S102, a positive determination is performed, and the flow proceeds to step S106.

In step S106, the control unit 40 causes the ray source drive unit 46 to move the radiation source 24 to an initial imaging position (imaging starting position).

In step S108, the control unit 40 compresses the breast N by moving the compression plate 26 toward the imaging surface 20 in response to a compression instruction given from the user by using the operation panel 48.

In a case where the breast N is compressed through the process in step S108, the user gives an exposure instruction by using the operation unit 72 from the console 50.

Therefore, in the next step S110, the control unit 40 determines whether or not there is an exposure instruction. A negative determination is performed until the exposure instruction is given, and a waiting state occurs. On the other hand, in a case where there is the exposure instruction, a positive determination is performed, and the flow proceeds to step S112.

In step S112, the control unit 40 acquires a position of the face F of the subject W from the face position detection sensor 35.

In the next step S114, the control unit 40 determines a movement speed and the like (including a movement speed, an acceleration section and acceleration, and a deceleration section and deceleration) of the radiation source 24 on the basis of the acquired position of the face F of the subject W. A position of the radiation source 24 may be defined by using a relative coordinate with a position of the face F of the subject W as a reference or an absolute coordinate having the origin at positions other than the face F. In a case of the relative coordinate, a position of the face F is the origin.

The radiation imaging apparatus 10 of the present embodiment performs control of a movement speed of the radiation source 24, such that a movement speed of the radiation source 24 in the vicinity of the face F of the subject W less than a movement speed of the radiation source 24 at other positions. The radiation imaging apparatus 10 of the present embodiment performs control of acceleration and deceleration (each of which is expressed by a change amount of a movement speed per unit time) of a movement speed of the radiation source 24 in the vicinity of the face F of the subject W less than acceleration and deceleration of a movement speed of the radiation source 24 in other positions. In the radiation imaging apparatus 10 of the present embodiment, movement speeds, accelerations, and decelerations of the radiation source 24 in the vicinity of the face F of the subject W and positions other than the vicinity of the face are stored in the storage unit 42 in advance.

In the radiation imaging apparatus 10 of the present embodiment, a position regarded as the vicinity of the face F of the subject W is defined in advance. For example, a position at which body motion of the subject W occurs due to the influence of movement of the radiation source 24 is obtained through a test or the like, and thus a range including the obtained position can be defined in advance as the vicinity of the face F of the subject W. A specific example of the position at which body motion of the subject W occurs may include a position within a range of ±3 degrees to ±10 degrees as an incidence angle range of the radiation source 24 with a central position of the face F of the subject W as a reference.

In the present embodiment, as an example, a position within a range of ±5 degrees which is an incidence angle range of the radiation source 24 with a central position of the face of the subject W as a reference is regarded as the vicinity of the face F of the subject W and is defined in advance.

Figure 6:
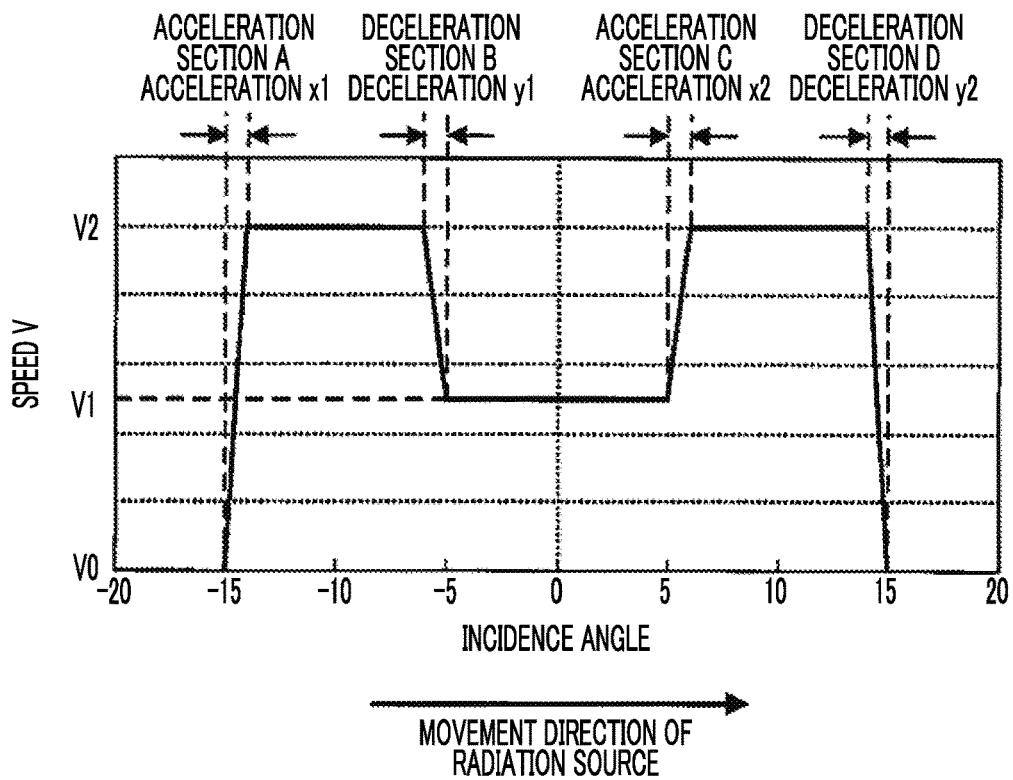
FIG. 6 is a timing chart illustrating an example of a relationship between an incidence angle and a movement speed of a radiation source in tomosynthesis imaging according to the first embodiment.

FIG. 6 is a timing chart illustrating an example of a relationship between an incidence angle and a movement speed of the radiation source 24 in tomosynthesis imaging of the present embodiment. In the timing chart shown in FIG. 6, a transverse axis expresses an incidence angle of the radiation R applied from the radiation source 24, and a longitudinal axis expresses a movement speed V of the radiation source 24. Hereinafter, a position of the radiation source 24 is expressed by an incidence angle of the radiation R.

In the example illustrated in FIG. 6, a position (central position) of the face F of the subject W is a position at which an incidence angle of the radiation R is 0 degrees. The example illustrated in FIG. 6 shows a case where an incidence angle range is ±15 degrees, an imaging starting position is −15 degrees, and an imaging ending position is +15 degrees.

In a case where an initial speed is indicated by v0, a target speed is indicated by vs, a movement distance is indicated by L, and acceleration (or deceleration) is indicated by β, a relationship of $vs^2 - v0^2 = 2L\beta$ is established. In the example illustrated in FIG. 6, an acceleration x1 in an acceleration section A is larger than an acceleration x2 in an acceleration section C (x1>x2>0). A deceleration y2 in a deceleration section D is larger than a deceleration y1 in a deceleration section B (y2>y1>0). The term "large deceleration" indicates that a change amount of a movement speed per unit time is large. The acceleration in the acceleration section A is the same as the deceleration in the deceleration section D (x1=y2), and the acceleration in the acceleration section C is the same as the deceleration in the deceleration section B (x2=y1).

In the next step S116, the control unit 40 causes the ray source drive unit 46 to start to move the radiation source 24.

In this case, first, the radiation source 24 starts to be moved toward an initial imaging position. In the example illustrated in FIG. 6, the radiation source 24 starts to be moved toward the imaging position corresponding to an incidence angle of −15 degrees.

Next, in step S118, the control unit 40 determines whether or not the radiation source 24 has been moved to the acceleration section. In the example illustrated in FIG. 6, the control unit 40 determines whether or not the radiation source is located in the acceleration section A or the acceleration section C. In a case where a positive determination is performed, the flow proceeds to step S120. In a case where the radiation source 24 starts to be moved from the imaging starting position (the imaging position corresponding to an incidence angle of −15 degrees), the position is included in the acceleration section A, and thus a positive determination is performed.

In step S120, the control unit 40 increases a movement speed of the radiation source 24 at the determined acceleration until the movement speed becomes the determined movement speed on the basis of the determination in the above step S114. As described above, the magnitudes of the accelerations are different from each other in the acceleration section A and the acceleration section C. Thus, the control unit 40 accelerates the radiation source on the basis of an acceleration corresponding to an acceleration section. In the acceleration section A, the movement speed is increased from a speed V0 (V0=0) to a speed V2 at the acceleration x1. In the acceleration section C, the movement speed is increased from a speed V1 to the speed V2 at the acceleration x2.

Next, in step S126, the control unit 40 determines whether or not the radiation source 24 has been moved to the next imaging position. In a case where the radiation source 24 has not been moved to the next imaging position yet, the flow returns to step S118.

On the other hand, in a case where a negative determination is performed in step S118, the flow proceeds to step S122. In step S122, the control unit 40 determines whether or not the radiation source 24 has been moved to a deceleration section. In the example illustrated in FIG. 6, the control unit 40 determines whether or not the radiation source 24 has been moved to the deceleration section B or the deceleration section D. In a case where a negative determination is performed, the flow proceeds to step S126. On the other hand, in a case where a positive determination is performed, the flow proceeds to step S124.

In step S124, the control unit 40 decreases a movement speed of the radiation source 24 on the basis of the deceleration determined in the above step S114, and then proceeds to step S126. As described above, the magnitudes of the decelerations are different from each other in the deceleration section B and the deceleration section D. Thus, the control unit 40 decelerates the radiation source on the basis of a deceleration corresponding to a deceleration section. In the deceleration section B, the movement speed is decreased from the speed V2 to the speed V1 at the deceleration y1. In the deceleration section D, the movement speed is decreased from the speed V2 to the speed V0 at the deceleration y2.

On the other hand, in a case where the radiation source 24 has been moved to the imaging position, a positive determination is performed in step S126, and the flow proceeds to step S128.

In step S128, the control unit 40 causes a projection image to be captured. Specifically, the control unit 40 performs control for applying the radiation R toward the breast N from the radiation source 24 and control for causing the radiation detector 30 to capture a projection image. A projection image generated through imaging in the radiation detector 30 undergoes necessary processes such as gain correction, offset correction, and defective pixel correction in the control unit 40, and is then stored in the storage unit 42 in correlation with an incidence angle of the radiation R. As a format of a projection image generated here, for example, an RAW image format is used.

In a case where the projection image has been captured, in the next step S130, the control unit 40 determines whether or not imaging (tomosynthesis imaging) is to be finished. In a case where projection images are not captured at all imaging positions, a negative determination is performed, and the flow returns to step S118. On the other hand, in a case where projection images are captured at all imaging positions, a positive determination is performed, and the flow proceeds to step S132.

In step S132, the control unit 40 cancels compression of the breast N in the compression plate 26. Specifically, the control unit 40 moves the compression plate 26 in a direction of becoming distant from the imaging surface 20 so as to cancel compression of the breast N, and then finishes the imaging process. In the radiation imaging system 1 of the present embodiment, in a case where the imaging process is finished in the radiation imaging apparatus 10, a radiation image (the projection image or the like stored in the storage unit 42) obtained through imaging is transmitted to the console 50 so as to be stored in the storage unit 62 of the console 50. The radiation image transmitted to the console 50 may be stored in the storage unit 42, and may be deleted from the storage unit 42.

In the radiation imaging system 1 of the present embodiment, a reconstructed image or a combined two-dimensional image can be generated by using the projection image captured by the radiation imaging apparatus 10. The "reconstructed image" in the present embodiment is also referred to as a tomographic image, and the tomographic image is reconstructed on the basis of a projection image. The "combined two-dimensional image" indicates a pseudo-two-dimensional image generated by combining projection images with each other.

Generation of a reconstructed image or a combined two-dimensional image using a projection image may be performed by any of the radiation imaging apparatus 10 or the console 50, and is not particularly limited. A generation method thereof is not particularly limited either, and, for example, a generation method of a reconstructed image may include a shift adding method or a well-known computed tomography (CT) reconstruction method of the related art. A generated reconstructed image or combined two-dimensional image may be stored in the storage unit 42 or the storage unit 62, may be displayed on the display unit 68, and may be output to an external device of the radiation imaging system 1.

In the present embodiment, a description has been made of a case where, with respect to a movement speed of the radiation source 24, the acceleration x1 is larger than the acceleration x2 (x1>x2), and the deceleration y2 is larger than the deceleration y1 (y2>y1), but the magnitudes of an acceleration and a deceleration are not limited to those in the present embodiment. For example, the acceleration x1 and the acceleration x2 may have the same magnitude (x1=x2). For example, the deceleration y1 and the deceleration y2 may have the same magnitude (y1=y2).

Figure 7:
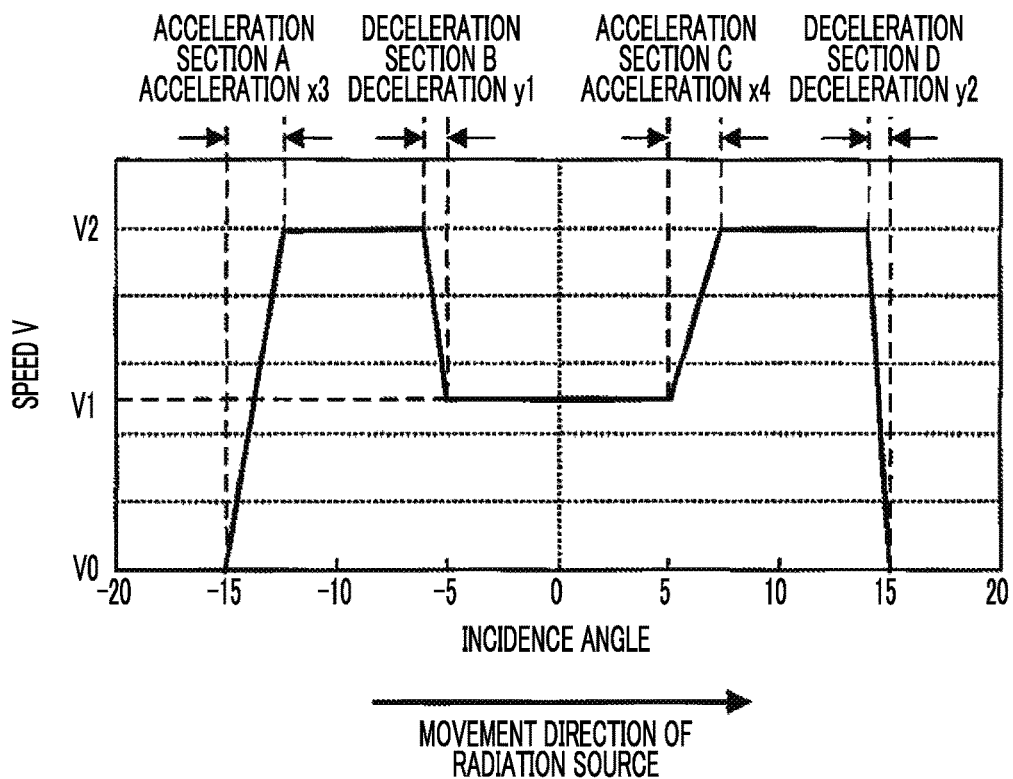
FIG. 7 is a timing chart illustrating another example of a relationship between an incidence angle and a movement speed of a radiation source in tomosynthesis imaging related to the first embodiment.

The subject W performs a reaction of being surprised in a case of acceleration in movement of the radiation source 24 compared with a case of deceleration, and thus there is concern that body motion may occur. Thus, an acceleration may be made smaller (delayed) than a deceleration, and thus an inclination of a speed for time may be made larger (steeper) in a case where deceleration is performed than in a case where acceleration is performed. FIG. 7 is a timing chart illustrating an example of a relationship between an incidence angle and a movement speed of the radiation source 24 in tomosynthesis imaging in this case. In the example illustrated in FIG. 7, the deceleration y1 in the deceleration section B and the deceleration y2 in the deceleration section D are the same as those in the case illustrated in FIG. 6. On the other hand, an acceleration x3 in the acceleration section A is smaller than the deceleration y2 and the acceleration x1 illustrated in FIG. 6 (x3<y2=x1). An acceleration x4 in the acceleration section C is smaller than the deceleration y1 and the acceleration x2 illustrated in FIG. 6 (x4<y1=x2). The acceleration x3 is larger than the acceleration x4 (x3>x4). Therefore, in the case illustrated in FIG. 7, a relationship of y2>y1>x3>x4 is obtained. The acceleration x3 may be the same as the deceleration y1 (x3=y1).

Second Embodiment

Next, a second embodiment will be described. The same portions as those of the radiation imaging system 1 and the radiation imaging apparatus 10 according to the first embodiment are given the same reference numerals, and detailed description thereof will be omitted. In a radiation imaging apparatus 10 of the present embodiment, a configuration of the radiation imaging apparatus 10 and an imaging process are different from those in the first embodiment.

Figure 8:
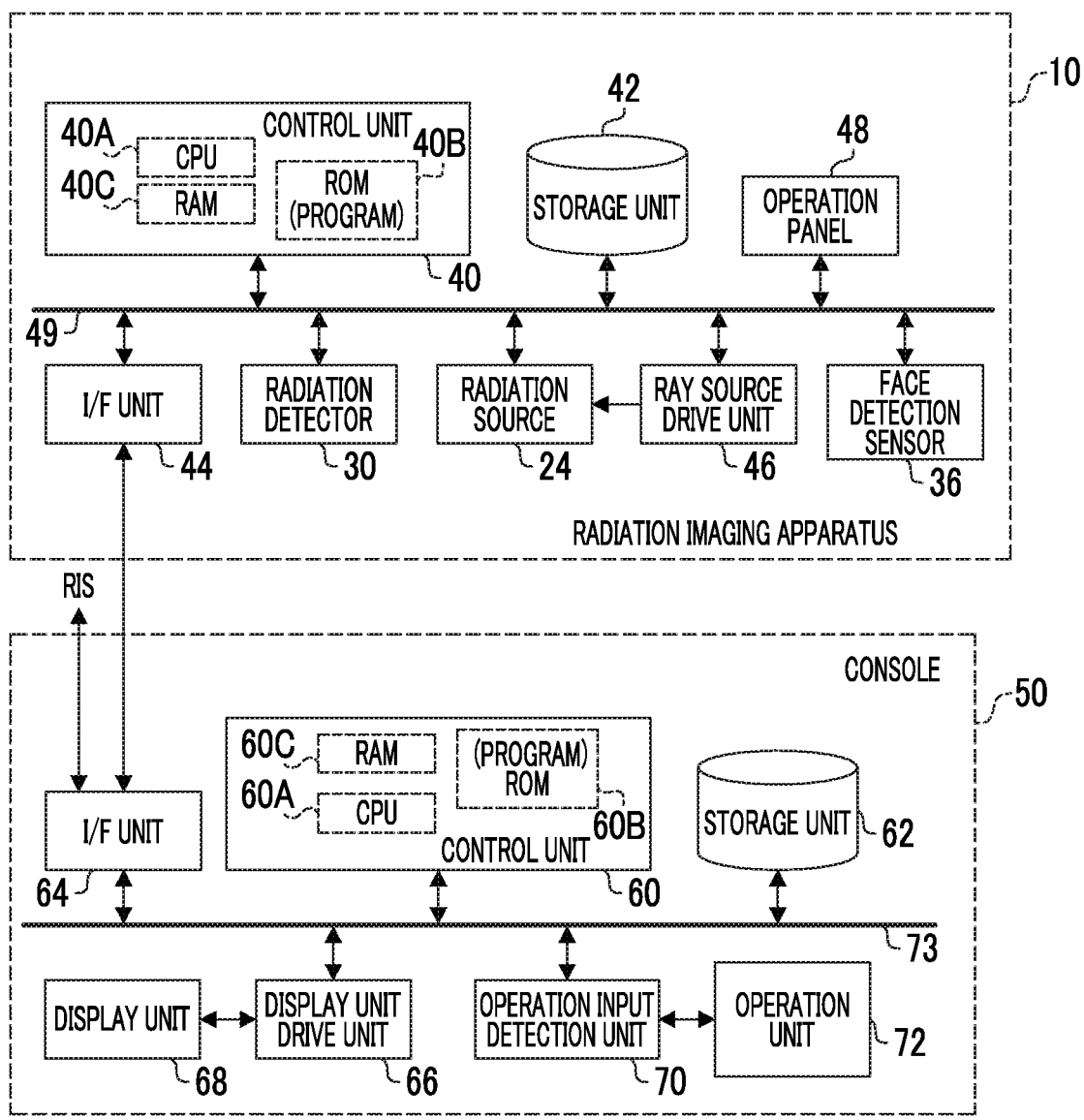
FIG. 8 is a block diagram illustrating a configuration example of a radiation imaging system according to a second embodiment.

FIG. 8 is a block diagram illustrating an example of a configuration of a radiation imaging system 1 of the present embodiment. As illustrated in FIG. 8, the radiation imaging apparatus 10 of the present embodiment includes a face detection sensor 36 instead of the face position detection sensor 35 of the radiation imaging apparatus 10 (refer to FIG. 4) of the first embodiment.

The face detection sensor 36 detects a position of the face F of the subject W facing the face guard 34 in the same manner as the face position detection sensor 35 of the first embodiment. The face detection sensor 36 detects a direction of the face F of the subject W. The face detection sensor 36 of the present embodiment uses a sensor, as an example, which captures a face image of the subject W with an imaging element in the same manner as the face position detection sensor 35 of the first embodiment, and detects a position and a direction of the face F of the subject W on the basis of the captured face image. The face detection sensor 36 is an example of a position detection unit and a direction detection unit of the present invention.

As a method of detecting a direction of the face F of the subject W, in addition to a detection method based on a face image, any of a thermal sensor, an ultrasonic sensor, or a microphone may be used. A detection method in a case of using the thermal sensor may include, for example, a method of detecting heat of exhaled breath of the subject W and determining a direction of the face F on the basis of a detected direction. A detection method in a case of using the ultrasonic sensor may include, for example, a method of detecting an ultrasonic wave reflected from the subject W, and determining of a direction of the face F by determining unevenness of the face F of the subject W on the basis of the ultrasonic wave. A detection method in a case of using the microphone may include, for example, a method of detecting voices (sounds) output from the subject W. and determining a direction of the face F on the basis of a detected direction.

Such techniques are only examples, and a technique in which a direction of the face F of the subject W can be determined is not particularly limited, and a combination of a plurality of techniques may be used, but a technique causing a less burden to be imposed on the subject W is preferably used.

Figure 9:
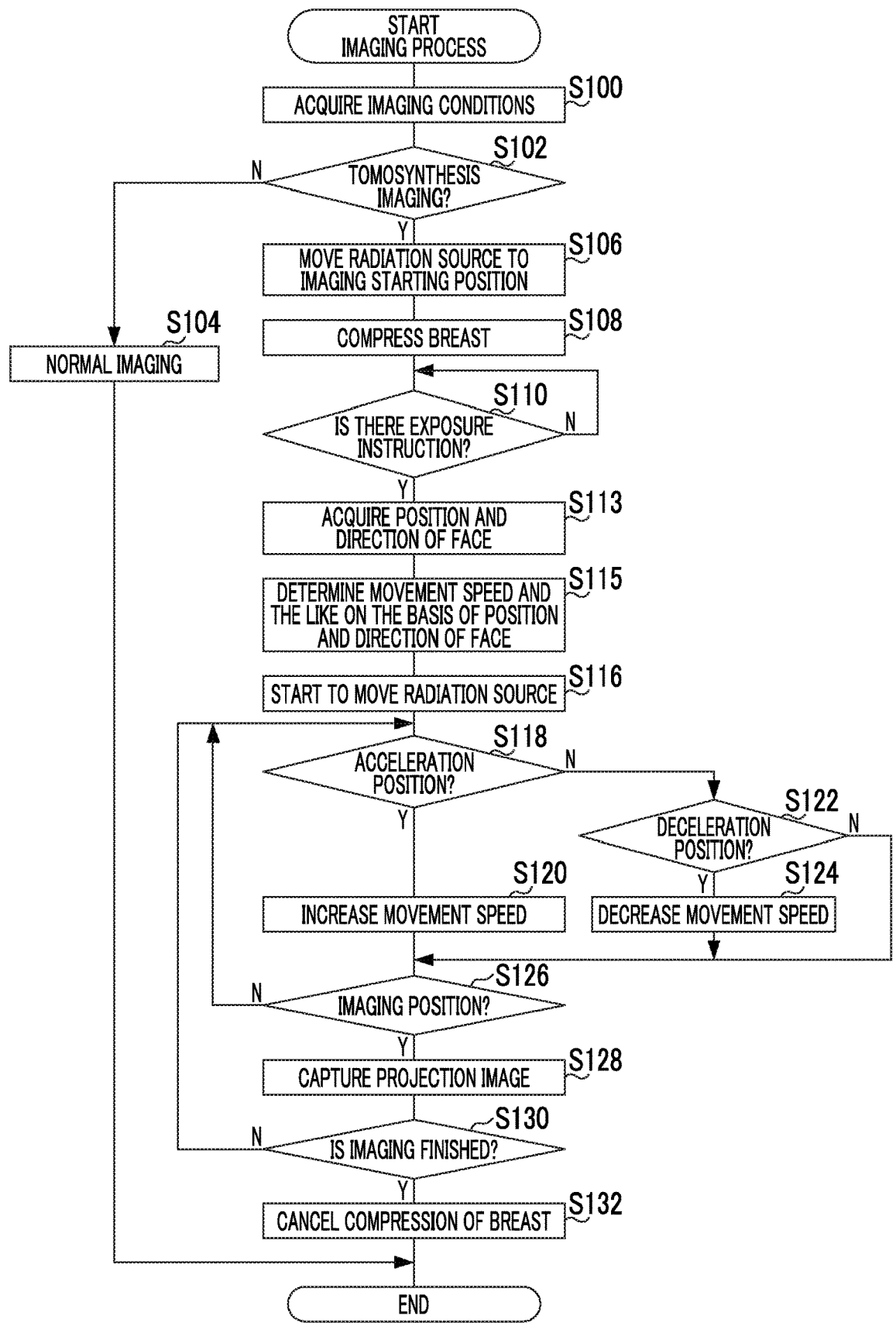
FIG. 9 is a flowchart illustrating an example of an imaging process performed in the radiation imaging apparatus according to the second embodiment.

Next, a description will be made of an operation of the radiation imaging apparatus 10 of the present embodiment with reference to the drawings. FIG. 9 is a flowchart illustrating an example of an imaging process performed by the control unit 40 of the radiation imaging apparatus 10 of the present embodiment. In the present embodiment, an imaging process performed by the radiation imaging apparatus 10 is partially different from the imaging process (refer to FIG. 5) of the first embodiment, and thus different processes will be described.

In the imaging process of the present embodiment illustrated in FIG. 9, steps S113 and S115 are executed instead of steps S112 and S114 in the imaging process (refer to FIG. 5) of the first embodiment.

In step S113, the control unit 40 acquires a position of the face F of the subject W and a direction of the face F from the face detection sensor 36.

In the next step S115, the control unit 40 determines a movement speed and the like (including a movement speed, an acceleration section and acceleration, and a deceleration section and deceleration) of the radiation source 24 on the basis of the acquired position of the face F of the subject W and direction of the face F.

In the same manner as in the first embodiment, the radiation imaging apparatus 10 of the present embodiment performs the control of the movement speed of the radiation source 24, such that the movement speed of the radiation source 24 is less in the vicinity of the face F of the subject W than at other positions.

The subject W performs a reaction of being surprised in a case where the moving radiation source 24 is viewed by the subject W compared with a case where the radiation source 24 is not viewed, and thus there is concern that body motion may occur. Thus, in the radiation imaging apparatus 10 of the present embodiment, an acceleration and a deceleration of a movement speed of the radiation source 24 are controlled according to a direction of the face F of the subject W. Specifically, an acceleration and a deceleration of a movement speed are made smaller (a change amount of the movement speed per unit time is made smaller) in a direction in which the face F of the subject W is directed than acceleration and deceleration of a movement speed in a direction in which the face is not directed.

In the radiation imaging apparatus 10 of the present embodiment, movement speeds, accelerations, and decelerations of the radiation source 24 in the vicinity of the face F of the subject W and positions other than the vicinity thereof according to a direction of the face F of the subject W are stored in the storage unit 42 in advance.

Figure 10:
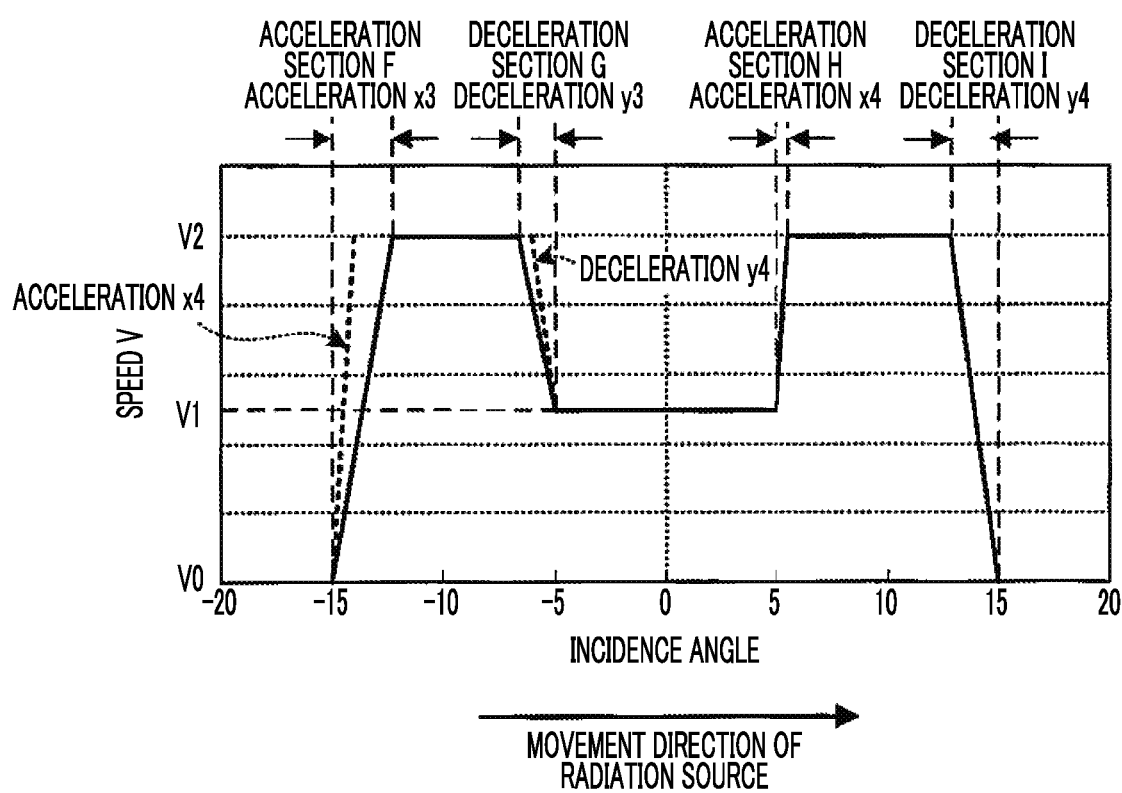
FIG. 10 is a timing chart illustrating an example of a relationship between an incidence angle and a movement speed of a radiation source in tomosynthesis imaging according to the second embodiment.

FIG. 10 is a timing chart illustrating an example of a relationship between an incidence angle and a movement speed of the radiation source 24 in tomosynthesis imaging of the present embodiment. In the example illustrated in FIG. 10, a position (central position) of the face F of the subject W is a position at which an incidence angle of the radiation R is 0 degrees. Specifically, a position of the face F is an in-plane position orthogonal to a plane including a straight line connecting the radiation source 24 at a position where an incidence angle of the radiation R is 0 degrees to the radiation detector 30 and including a movement position of the radiation source 24. During imaging, the face F of the subject W is directed toward an imaging starting position (an imaging position corresponding to an incidence angle of −15 degrees) of the radiation source 24.

In the same manner as in the example illustrated in FIG. 6, the example illustrated in FIG. 10 shows a case where an incidence angle range is ±15 degrees, an imaging starting position is −15 degrees, and an imaging ending position is +15 degrees.

In the example illustrated in FIG. 10, an acceleration x3 in an acceleration section F is smaller than an acceleration x4 in an acceleration section H (0<x3<x4). A deceleration y3 in a deceleration section G is smaller than a deceleration y4 in a deceleration section 1 (0<y3<y4).

In the radiation imaging apparatus 10 of the present embodiment, in processes in step S116 and the subsequent steps, the control unit 40 controls movement of the radiation source 24 on the basis of the movement speed determined in step S115. As mentioned above, in the radiation imaging apparatus 10 of the present embodiment, movement of the radiation source 24 is controlled on the basis of a position of the face F of the subject W and a direction of the face F.

Body motion of the subject W tends to occur in a case where the radiation source 24 comes close to the subject more than in a case where the radiation source 24 becomes distant from the subject. Thus, control may be performed such that an acceleration and a deceleration are made smaller in a case where a direction of the face F of the subject W is directed toward the imaging starting position than in a case where the face is directed toward the imaging stoppage position.

Third Embodiment

Next, a third embodiment will be described. The same portions as those of the radiation imaging system 1 and the radiation imaging apparatus 10 according to the first embodiment are given the same reference numerals, and detailed description thereof will be omitted.

Configurations of the radiation imaging system 1 and the radiation imaging apparatus 10 are the same as those of the radiation imaging system 1 and the radiation imaging apparatus 10 of the first embodiment (refer to FIGS. 1 to 4), and thus description thereof will be omitted.

In the first embodiment, a description has been made of a case where a projection image is captured at imaging position while moving the radiation source 24 from the imaging starting position to the imaging stoppage position. In contrast, in the present embodiment, a description will be made of a case where movement of the radiation source 24 is stopped at each imaging position, and a projection image is captured by irradiating the breast N with the radiation R in a state in which the radiation source 24 is stopped. Therefore, in the radiation imaging apparatus 10 of the present embodiment, an imaging process is partially different from the imaging process (refer to FIG. 5) of the first embodiment, and thus different processes will be described.

Figure 11:
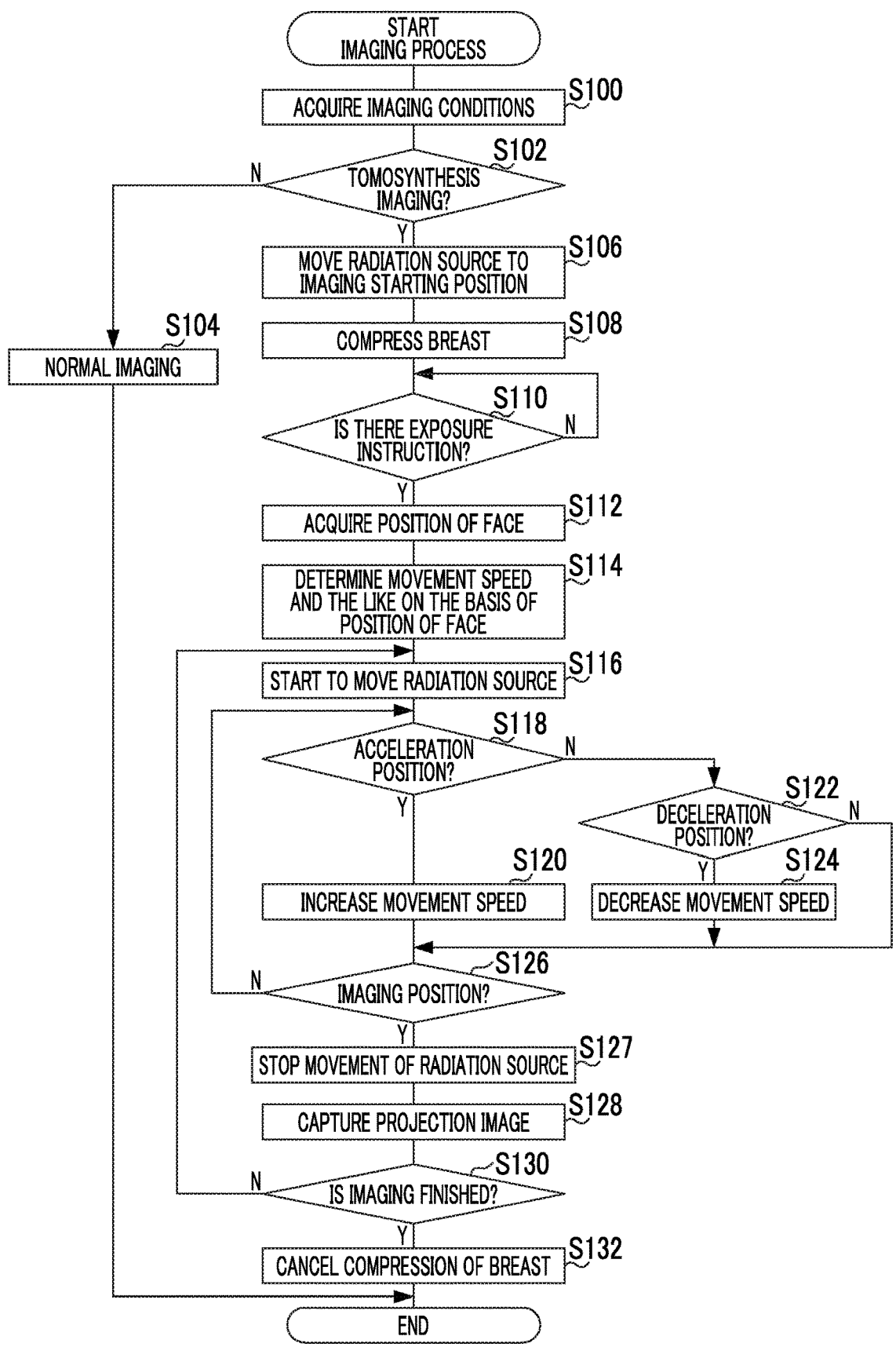
FIG. 11 is a flowchart illustrating an example of an imaging process performed in a control unit of a radiation imaging apparatus according to a third embodiment.

FIG. 11 is a flowchart illustrating an example of a flow of an imaging process performed by the control unit 40 of the radiation imaging apparatus 10 of the present embodiment.

In the imaging process of the present embodiment illustrated in FIG. 11, in the same manner as in the imaging position (refer to FIG. 5) of the first embodiment, in step S114, the control unit 40 determines a movement speed and the like (including a movement speed, an acceleration section and acceleration, and a deceleration section and deceleration) of the radiation source 24 on the basis of a position of the face F of the subject W, but stops the radiation source 24 at each imaging position.

Figure 12:
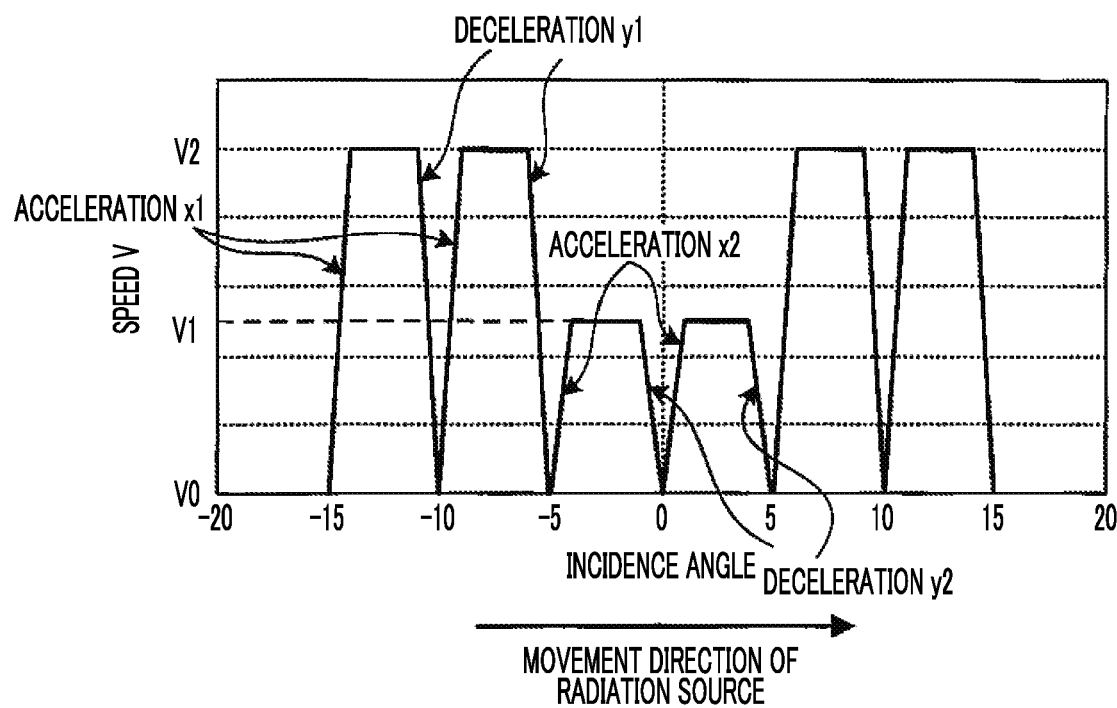
FIG. 12 is a timing chart illustrating an example of a relationship between an incidence angle and a movement speed of a radiation source in tomosynthesis imaging according to the third embodiment.

FIG. 12 is a timing chart illustrating an example of a relationship between an incidence angle and a movement speed of the radiation source 24 in tomosynthesis imaging of the present embodiment. The example illustrated in FIG. 12 shows a case where an imaging position is −15 degrees (imaging starting position), −10 degrees, 5 degrees, 0 degrees, +5 degrees, +10 degrees, and +15 degrees (imaging stoppage position).

In the imaging process of the present embodiment illustrated in FIG. 11, step S127 is added between step S126 and step S128 in the imaging process (refer to FIG. 5) of the first embodiment.

In the present embodiment, in a case where the radiation source reaches an imaging position, a positive determination is performed in step S126, and the flow proceeds to step S127. In step S127, the control unit 40 causes the ray source drive unit 46 to stop movement of the radiation source 24. In the next step S128, the control unit 40 captures a projection image a state in which movement of the radiation source 24 is stopped.

The imaging process of the present embodiment is different from the imaging process (refer to FIG. 5) of the first embodiment in that the flow returns to step S116 in a case where it is determined that imaging is not finished in step S130. In the present embodiment, the flow returns to step S116, and thus the stopped radiation source 24 starts to be moved again.

As mentioned above, in the present embodiment, since movement of the radiation source 24 is stopped at each imaging position, increasing and decreasing of a movement speed of the radiation source 24 are repeatedly performed at each imaging position.

In the example illustrated in FIG. 12, the acceleration x1 and the deceleration y1 are used as an acceleration and a deceleration of the radiation source 24 at positions (positions corresponding to incidence angles of −15 degrees to −5 degrees, and +5 degrees to +15 degrees) other than the vicinity of the face F of the subject W. The acceleration x2 and the deceleration y2 are used as an acceleration and a deceleration of the radiation source 24 in the vicinity (a position corresponding to an incidence angle of −5 degrees to +5 degrees) of the face F of the subject W.

The example illustrated in FIG. 12 shows a case where a change amount per unit time is linear (constant) as a pattern of increasing and decreasing of a movement speed of the radiation source 24, but a change pattern of a movement speed is not limited thereto. For example, change patterns of a movement speed may be different from each other in the vicinity of the face F of the subject W and positions other than the vicinity thereof. For example, in the vicinity of the face F of the subject W, as in an example illustrated in FIG. 13, a change pattern (acceleration) of a movement speed in a case where acceleration is performed may be an S-shaped drive pattern (speed V=V1(1−cos θ) where θ is any value)). A change pattern of a movement speed in a case where deceleration is performed may be the same as above. In the example illustrated in FIG. 13, a movement speed of the radiation source 24 more slowly changes in the vicinity of the face F of the subject W than at positions other than the vicinity thereof.

Figure 13:
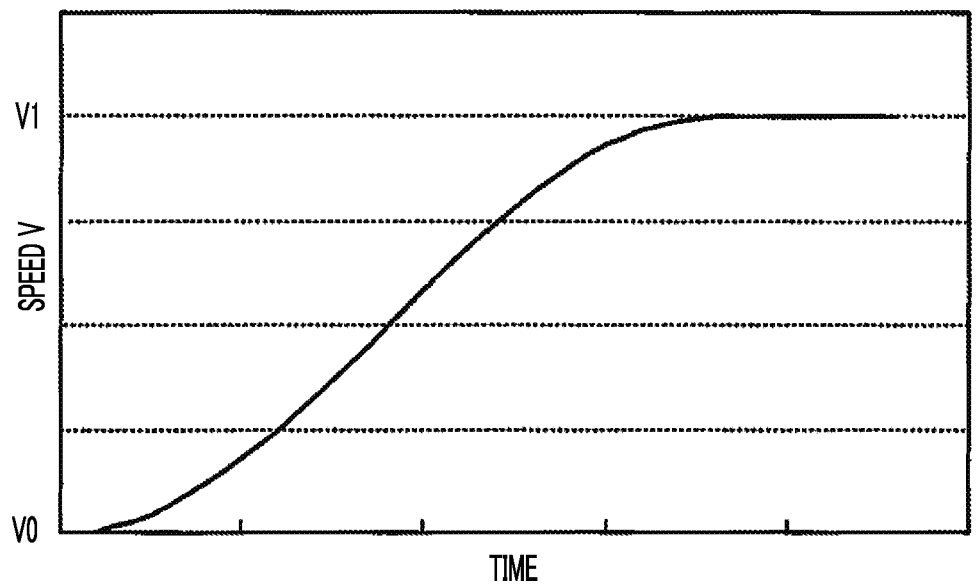
FIG. 13 is a graph for explaining a change pattern of a movement speed in a case where the movement speed of the radiation source is increased in the third embodiment.

The present embodiment is not limited to the example illustrated in FIG. 13, and, for example, a movement speed may change stepwise in the vicinity of the face F of the subject W. As a specific example of a case where a movement speed of the radiation source 24 is increased, two-stage control is performed in which a movement speed is changed to a speed lower (slower) than the speed V1 illustrated in FIG. 13, and is then changed to the speed V1 at an acceleration smaller than the acceleration x2.

As described above, the control unit 40 of the radiation imaging apparatus 10 of above-described respective embodiments performs control of moving the radiation source 24, and emitting the radiation R from the radiation source 24 at a plurality of positions at which incidence angles of the radiation R to the breast N of the subject W are different from each other. The control unit 40 controls the radiation detector 30 to detect the radiation R emitted from the radiation source 24 at a plurality of positions. The control unit 40 performs control of moving the radiation source 24 at a movement speed corresponding to a position of the radiation source 24 relative to a subject face proximate position.

In the radiation imaging apparatus 10 of above-described respective embodiments, in a case where tomosynthesis imaging is performed, a movement speed of the radiation source 24 is reduced in the vicinity of the face F of the subject W more than a movement speed of the radiation source 24 at positions other than the vicinity thereof. An acceleration and a deceleration of a movement speed of the radiation source 24 are reduced (a change amount of the movement speed per unit time is smaller) in the vicinity of the face F of the subject W more than an acceleration and a deceleration of a movement speed of the radiation source 24 at positions other than the vicinity thereof. Consequently, it is possible to prevent body motion of the subject W due to being surprised at movement of the radiation source 24. Therefore, according to the radiation imaging apparatus 10 of above-described respective embodiments, it is possible to suppress deterioration in image quality of a radiation image (such as a reconstructed image or a combined two-dimensional image) due to body motion of the subject W.

In the radiation imaging apparatus 10 of above-described respective embodiments, the face guard 34 is moved along with the radiation source 24. Thus, a mechanism of the radiation imaging apparatus 10 or the face guard 34 can be easily configured compared with a case where a position of the face guard is fixed without being moved, and an attitude of the subject W is stabilized by bringing the face F of the subject W into contact with the face guard.

In the above-described respective embodiments, a position of the face F of the subject W is detected by the face position detection sensor 35 or the face detection sensor 36, and a movement speed of the radiation source 24 is determined on the basis of the detected position of the face F (refer to step S114 in FIGS. 5 and 11, and step S115 in FIG. 9). However, as described above, in a case where tomosynthesis imaging is performed, the face F of the subject W is often located at a position corresponding to an incidence angle of 0 degrees. Thus, the control unit 40 may change a movement speed of the radiation source 24 according to a position of the radiation source 24 for the position corresponding to 0 degrees.

In other words, the control unit 40 performs control such that a movement speed of the radiation source 24 is changed, and the radiation source 24 is moved, according to a position of the radiation source 24 for a position (a position of an incidence angle of 0 degrees) in a normal direction to the detection surface 31 of the radiation detector 30 on an opposite side to the radiation source 24 with the breast N of the subject W interposed therebetween, and incidence angles of the radiation R to the breast N from the radiation source 24 are a plurality of angles including 0 degrees (an example of a first angle of the present invention) as an angle of the normal direction to the detection surface 31 and angles (examples of second angles of the present invention) which are different from 0 degrees. The control unit 40 controls the radiation detector 30 to capture a projection image (radiation image) of the breast N at an imaging position corresponding to an incidence angle of the radiation R.

A position or a direction of the face F of the subject W may be detected on the basis of imaging conditions or object information included in an imaging menu. For example, a position or a direction of the face F of the subject W may be detected on the basis of a position or an inclination of the compression plate 26. In many cases, the face F is directed toward the left if the right breast N is imaged, and the face F is directed toward the right if the left breast N is imaged. Therefore, a position or a direction of the face F of the subject W may be detected depending on whether the breast N of the subject W is the right or left breast N.

In the imaging process of the above-described respective embodiments, the radiation source 24 is moved to the imaging starting position, and then the breast N of the subject W is compressed with the compression plate 26 so as to be positioned, but the breast N may be compressed, and then the radiation source 24 may be moved to the imaging starting position. Since the subject W is positioned, and then the radiation source 24 is moved to the imaging starting position, body motion may occur in the subject W as described above. In this case, the influence exerted on a radiation image (projection image) is small even if the body of the subject W moves since imaging is not performed, but there is concern that a position of the breast N may be deviated relative to a position positioned by the user. Thus, as described in the above-described respective embodiments, preferably, control is performed such that a movement speed of the radiation source 24 is reduced in the vicinity of the face F of the subject W more than a movement speed of the radiation source 24 at positions other than the vicinity thereof.

The above-described respective embodiments may be combined with each other. For example, a case where movement of the radiation source 24 is stopped at an imaging position, and a projection image is captured as in the radiation imaging apparatus 10 of the third embodiment may be combined with control corresponding to a direction of the face F of the subject W as in the radiation imaging apparatus 10 of the second embodiment.

In the above-described respective embodiments, a description has been made of a case where the radiation imaging apparatus 10 has functions of the ray source control unit and the detector control unit, but the console 50 or an external control device which is different from the radiation imaging apparatus 10 and the console 50 may have some of the functions of the respective units or all of the functions.

In the radiation imaging apparatus 10 of the above-described respective embodiments, the breast N of the subject W is used as an object, but an object is not limited to the breast N. and may be, for example, other parts of a human body, or living things or objects (inorganic substances) other than a human.

The radiation R of the above-described respective embodiments is not particularly limited, and may be an X-ray or a γ-ray.

The configurations, the operations, and the like of the radiation imaging system 1, the radiation imaging apparatus 10, and the console 50 described in the above-described respective embodiments are only examples, and may be changed depending on situations within the scope without departing from the spirit of the present invention.

EXPLANATION OF REFERENCES

1: radiation imaging system
10: radiation imaging apparatus
24: radiation source
30: radiation detector
31: detection surface
35: face position detection sensor
36: face detection sensor
40, 60: control unit
50: console
W: subject
N: breast

What is claimed is:

1. A control device of a mammography comprising:
a ray source control unit that performs control of moving a radiation source, and emitting radiation from the radiation source at a plurality of positions at which incidence angles of radiation to a breast of a subject are different from each other; and
a detector control unit that performs control of causing a radiation detector to detect radiation emitted from the radiation source at the plurality of positions,
wherein the ray source control unit performs control of moving the radiation source at a movement speed corresponding to a position of the radiation source relative to a subject face proximate position.

2. The control device of a mammography according to claim 1,
wherein, in a case where the movement speed is changed, the ray source control unit performs control of the movement speed of the radiation source, such that the movement speed of the radiation source or a change amount of the movement speed per unit time is less at a position of the radiation source that has been predefined as a position near the subject face proximate position than at other positions.

3. The control device of a mammography according to claim 2,
wherein the ray source control unit performs the control such that speed change patterns of the radiation source are different from each other at the predefined position of the radiation source and other positions.

4. The control device of the mammography according to claim 1, further comprising:
a position detection unit that detects a position of the face of the subject,
wherein the ray source control unit changes the movement speed of the radiation source according to a position of the radiation source for the position of the face of the subject on the basis of a detection result in the position detection unit, and moves the radiation source.

5. The control device of the mammography according to claim 2, further comprising:
a position detection unit that detects a position of the face of the subject,
wherein the ray source control unit changes the movement speed of the radiation source according to a position of the radiation source for the position of the face of the subject on the basis of a detection result in the position detection unit, and moves the radiation source.

6. The control device of the mammography according to claim 3, further comprising:
a position detection unit that detects a position of the face of the subject,
wherein the ray source control unit changes the movement speed of the radiation source according to a position of the radiation source for the position of the face of the subject on the basis of a detection result in the position detection unit, and moves the radiation source.

7. The control device of the mammography according to claim 1,
wherein the ray source control unit sets the plurality of positions to positions corresponding to a plurality of angles including a first angle as an angle of a normal direction to a detection surface of the radiation detector and a second angle which is different from the first angle.

8. The control device of the mammography according to claim 2,
wherein the ray source control unit sets the plurality of positions to positions corresponding to a plurality of angles including a first angle as an angle of a normal direction to a detection surface of the radiation detector and a second angle which is different from the first angle.

9. The control device of the mammography according to claim 3,
wherein the ray source control unit sets the plurality of positions to positions corresponding to a plurality of angles including a first angle as an angle of a normal direction to a detection surface of the radiation detector and a second angle which is different from the first angle.

10. The control device of the mammography according to claim 4,
wherein the ray source control unit sets the plurality of positions to positions corresponding to a plurality of angles including a first angle as an angle of a normal direction to a detection surface of the radiation detector and a second angle which is different from the first angle.

11. The control device of the mammography according to claim 5,
wherein the ray source control unit sets the plurality of positions to positions corresponding to a plurality of angles including a first angle as an angle of a normal direction to a detection surface of the radiation detector and a second angle which is different from the first angle.

12. The control device of the mammography according to claim 6,
wherein the ray source control unit sets the plurality of positions to positions corresponding to a plurality of angles including a first angle as an angle of a normal direction to a detection surface of the radiation detector and a second angle which is different from the first angle.

13. The control device of the mammography according to claim 7,
wherein, in a case where the movement speed is changed, the ray source control unit performs the control of the movement speed of the radiation source, such that the movement speed of the radiation source or a change amount of the movement speed per unit time is less in a case where the radiation source is located at a position within a predetermined range which has been predefined and in which the incidence angle includes the first angle than in a case where the radiation source is located at other positions.

14. The control device of the mammography according to claim 13,
wherein the ray source control unit performs the control such that a speed change pattern of the radiation source in a case where the radiation source is located at the position within the predetermined range is different from a speed change pattern of the radiation source in a case where the radiation source is located at other positions.

15. The control device of the mammography according to claim 1,
wherein, in a case where the movement speed is changed by changing a change amount of the movement speed per unit time, the ray source control unit sets an absolute value of the change amount in a case where acceleration is performed to be smaller than an absolute value of the change amount in a case where deceleration is performed.

16. The control device of the mammography according to claim 1, further comprising:
a direction detection unit that detects a direction of the face of the subject,
wherein the ray source control unit performs at least one of control of the movement speed on the basis of a detection result in the direction detection unit such that the movement speed is less in a direction in which the face of the subject is directed than in a direction in which the face of the subject is not directed, or control of setting an absolute value of a change amount in a case where acceleration is performed in a direction in which the face of the subject is directed to be smaller than an absolute value of the change amount in a case where deceleration is performed in a direction in which the face of the subject is not directed if the movement speed is changed by changing the change amount of the movement speed per unit time.

17. The control device of the mammography according to claim 1,
wherein the ray source control unit stops movement of the radiation source at each imaging position corresponding to the incidence angle of the radiation source.

18. A mammography comprising:
a radiation source that irradiates an object with radiation;
a radiation detector that captures a radiation image of the object on the basis of radiation having been transmitted through the object; and
the control device of the mammography according to claim 1.

19. A radiation imaging method of a mammography of causing a computer to execute and causing the computer to function as the control device of the mammography according to claim 1, a process comprising:
performing control of moving a radiation source, and emitting radiation from the radiation source at a plurality of positions at which incidence angles of radiation to a breast of a subject are different from each other;
performing control of causing a radiation detector to detect radiation emitted from the radiation source at the plurality of positions; and
performing control of moving the radiation source at a movement speed corresponding to a position of the radiation source relative to a subject face proximate position.

20. A non-transitory computer readable recording medium storing a radiation imaging program of a mammography for causing a computer to execute and causing the computer to function as the control device of the mammography according to claim 1, a process comprising:
performing control of moving a radiation source, and emitting radiation from the radiation source at a plurality of positions at which incidence angles of radiation to a breast of a subject are different from each other;
performing control of causing a radiation detector to detect radiation emitted from the radiation source at the plurality of positions; and
performing control of moving the radiation source at a movement speed corresponding to a position of the radiation source relative to a subject face proximate position.

* * * * *